United States Patent [19]

Wrede et al.

[11] Patent Number: 6,140,303
[45] Date of Patent: *Oct. 31, 2000

[54] FRAGRANCE-CONTAINING PREPARATION

[75] Inventors: Wolfgang Wrede, Holzminden; Jörg Dröge, Rühle, both of Germany

[73] Assignee: Haarmann & Reimer GmbH, Holzminden, Germany

[*] Notice: This patent issued on a continued prosecution application filed under 37 CFR 1.53(d), and is subject to the twenty year patent term provisions of 35 U.S.C. 154(a)(2).

[21] Appl. No.: 09/135,752

[22] Filed: Aug. 18, 1998

[30] Foreign Application Priority Data

Sep. 8, 1997 [DE] Germany .............................. 197 39 204

[51] Int. Cl.$^7$ ...................................................... A61K 7/46
[52] U.S. Cl. ............................. 512/2; 424/76.2; 424/76.3; 424/76.4
[58] Field of Search ............................... 512/2; 424/76.2, 424/76.3, 76.4

[56] References Cited

U.S. PATENT DOCUMENTS

| | | | |
|---|---|---|---|
| 4,322,400 | 3/1982 | Yuhas . | |
| 4,617,390 | 10/1986 | Hoppe et al. | 544/197 |
| 4,724,137 | 2/1988 | Hoppe et al. | 424/59 |
| 5,165,915 | 11/1992 | Tokubo et al. | 424/63 |
| 5,324,490 | 6/1994 | Van Vlahakis et al. | 422/305 |
| 5,553,630 | 9/1996 | Dupuis et al. | 132/202 |
| 5,688,831 | 11/1997 | El-Nokaly et al. | 424/59 |
| 5,690,917 | 11/1997 | Eteve et al. | 424/60 |
| 5,798,108 | 8/1998 | Nadaud et al. | 424/401 |
| 5,863,522 | 1/1999 | Forestier et al. | 424/59 |

FOREIGN PATENT DOCUMENTS

| | | |
|---|---|---|
| 0 194 017 | 9/1986 | European Pat. Off. . |
| 0 536 444 | 4/1993 | European Pat. Off. . |
| 2680684-A1 | 3/1993 | France . |
| 2335111 | 1/1974 | Germany . |
| 3729381A1 | 3/1988 | Germany . |

Primary Examiner—Monique T. Cole
Attorney, Agent, or Firm—Brinks Hofer Gilson & Lione

[57] ABSTRACT

The invention relates to a preparation which comprises perfume, polymer, aluminium stearate and essentially water. This gives a product which can be produced very easily at low cost and which has an unexpectedly linear fragrance release over a period of more than four weeks.

4 Claims, No Drawings

FRAGRANCE-CONTAINING PREPARATION

BACKGROUND OF THE INVENTION

1. Field of the Invention

The invention relates to a fragrance-containing preparation which, when in use, gives off fragrances into the environment, meaning that it can be used as an air freshener. For the purposes of the invention, air fresheners are products which vaporize fragrances even at room temperature (without additional energy input) and thus perfume the surrounding air.

2. Discussion of the Background

Liquid air fresheners are known (e.g. EP-A 194 017 (U.S. Pat. No. 4,663,081), and 536 444) but, because there is a danger they may leak, they require expensive packaging and careful handling during use. There have thus already been attempts in the past to overcome these disadvantages by using air fresheners in the form of soft gels or pastes of relatively high viscosity (e.g. U.S. Pat. No. 5,324,490). Such products are normally prepared by mixing a perfume oil emulsion and a viscosity-increasing component. Gel-like or paste-like air fresheners do, however, need to satisfy many requirements.

The viscosity-increasing component should be effective in as small an amount as possible, be able to be stirred into the perfume oil emulsion at room temperature, impede evaporation of the perfume oil components as little as possible and, above all, permit as linear an evaporation of the individual perfume oil components as possible, that is, the composition of the evaporating fragrances should be as constant as possible.

The air fresheners themselves should not melt up to temperatures of 60° C.; in addition, they should not have a tendency towards uncontrolled migration of the aqueous phase and definitely not towards synaeresis (even upon cooling); thus, no clearly visible liquid should separate out on the air freshener. Volume shrinkage during use is accepted or even desired because it indicates the reduction in the life of the air fresheners.

No air fresheners which satsify all of the stated requirements are known to date. The object of the invention was thus to provide such improved air fresheners.

SUMMARY OF THE INVENTION

Surprisingly, it has now been found that preparations satisfy the abovementioned conditions if the thickener used comprises polymers and aluminium stearate. For the purposes of the invention, "aluminium stearate" is taken to mean aluminium mono-, di- and tristearates.

The novel preparations can be used without classical emulsifiers. In this respect, the term "polymer" does not include anionic emulsifiers, cationic emulsifiers and non-ionic emulsifiers (such as polyethers).

DESCRIPTION OF THE INVENTION

The invention thus provides an aqueous preparation comprising

A. polymer,

B. aluminium stearate and

C. perfume.

Preferred polymers A include self-emulsifying vinyl polymers, acrylic and methacrylic polymers, polyamides, polyimines and polycarboxylic acids, particular preference being given to polyacrylamides.

Polymer A can be dissolved in water and the resulting solution dispersed in suitable hydrocarbons. $C_{12}$–$C_{24}$-1-isoolefins have proven to be particularly suitable.

The novel preparations preferably comprise from 0.01 to 5 parts by weight of polymer, from 1 to 20 parts by weight of perfume, from 0.1 to 1 part by weight of aluminium stearate and from 84 to 97.9 parts by weight of water.

The preparations can be prepared by firstly stirring the perfume into the initial charge of water. When the droplets have become sufficiently small, which is the case after a short stirring time using normal stirrers, the polymer and the aluminium stearate are slowly added until the desired consistency is obtained. The consistency is stably creamy and barely flowable. The preparations are characterized by an extraordinarily linear evaporation of the perfume over a period of at least 4 weeks.

The novel preparations may comprise colorants and preservatives in customary amounts.

The examples below illustrate the invention.

The percentages in the examples are in each case by weight; parts are parts by weight.

EXAMPLES

Example 1

10 parts of perfume oil (e.g. citrus, lemon, orange or floral) were stirred into 87 parts of water. Stirring was continued until the perfume oil droplets were a constant size (very small, but still visible to the naked eye). Three parts of the emulsion of an aqueous polyacrylamide solution in 1-isoolefins (®SOLAGUM SH 210 from SEPPIC, Paris; solids content about 46%) were slowly stirred into this emulsion to give a stable creamy consistency (barely flowable).

During storage, 80 g samples showed a weight loss of 30% after two weeks and 60% after four weeks. The odor after four weeks could not be differentiated from the odor of fresh samples; this means that all of the fragrance components had evaporated to the same extent.

Example 2

Example 1 was repeated except that instead of 10 parts of perfume oil and 3 parts of SOLAGUM SH 210, only 5 parts of perfume oil and 5 parts of SOLAGUM SH 210 were used. The results were as in Example 1.

Examples 3 and 4

Examples 1 and 2 were carried out using ®Solagum SJ 108 from SEPPIC, Paris (solids content about 30%) instead of Solagum SH 210. The results resembled the results of Examples 1 and 2.

In all of the test cases, it has been shown that the presence of aluminium stearate significantly influenced neither the fragrance quality nor the course of the weight loss curves.

We claim:

1. An aqueous air-freshening preparation having a stable creamy consistency, comprising: from 84 to 97.9 parts by weight of water; from 0.01 to 5 parts by weight of a water-soluble polymer selected from the group consisting of methacrylic polymer, polyamide, polyimine, polycarboxylic acid, polyacrylamide, and mixtures thereof, from 0.1 to 1 part by weight of aluminum stearate; and from 1 to 20 parts by weight of the perfume oil; the weights being based in each case on 100 parts by weight of the total weight of the preparation.

2. The preparation of claim 1 wherein the perfume oil is selected from the group consisting of citrus extract, lemon extract, orange extract, and floral extract, and mixtures thereof.

3. The preparation of claim 1 wherein the preparation further comprises a colorant, or a preservative, or both.

4. The preparation of claim 1 wherein the preparation emits fragrance through the evaporation of water and perfume from the preparation into air.

* * * * *